United States Patent [19]

Richardson et al.

[11] Patent Number: 4,797,406

[45] Date of Patent: Jan. 10, 1989

[54] AMIDES AND ESTERS CONTAINING BRIDGED PIPERIDINES AND USE AS SEROTONIN M ANTAGONISTS

[75] Inventors: Brian P. Richardson, Magden, Switzerland; Günter Engel, Weil, Fed. Rep. of Germany; Rudolf K. A. Giger, Riehen; Andrea Vasella, Meilen, both of Switzerland

[73] Assignee: Sandoz Ltd., Basel, Switzerland

[21] Appl. No.: 874,756

[22] Filed: Jun. 16, 1986

Related U.S. Application Data

[63] Continuation of Ser. No. 644,810, Aug. 27, 1984, abandoned.

[30] Foreign Application Priority Data

Aug. 26, 1983 [CH] Switzerland ............ 4675/83
Nov. 3, 1983 [CH] Switzerland ............ 5933/83
Dec. 23, 1983 [CH] Switzerland ............ 6877/83

[51] Int. Cl.$^4$ .............. A61K 31/445; C07D 401/12; C07D 405/12; C07D 221/22
[52] U.S. Cl. .................... 514/299; 546/112; 546/183
[58] Field of Search ............ 546/112, 183; 514/299

[56] References Cited

U.S. PATENT DOCUMENTS

| | | | |
|---|---|---|---|
| 2,748,134 | 5/1956 | Stoll et al. | 546/193 |
| 3,170,927 | 2/1965 | Nádor et al. | 546/129 |
| 3,342,826 | 9/1967 | Miller et al. | 546/224 |
| 3,405,134 | 10/1968 | Judd | 546/133 |
| 3,702,324 | 11/1972 | Skinner et al. | 546/133 |
| 3,741,973 | 6/1973 | Fonken et al. | 546/112 X |
| 4,089,960 | 5/1978 | Gosteli et al. | 546/133 X |
| 4,093,734 | 6/1978 | Krüger et al. | 544/165 X |
| 4,213,983 | 7/1980 | Hadley et al. | 546/93 X |
| 4,273,778 | 6/1981 | Hadley et al. | 546/112 X |
| 4,459,300 | 7/1984 | Watts | 546/124 X |
| 4,499,099 | 2/1985 | Watts | 546/112 X |

FOREIGN PATENT DOCUMENTS

| | | | |
|---|---|---|---|
| 42705 | 12/1981 | European Pat. Off. | 514/161 |
| 67770 | 12/1982 | European Pat. Off. | 546/124 |
| 68700 | 1/1983 | European Pat. Off. | 514/161 |
| 76592 | 4/1983 | European Pat. Off. | 514/161 |
| 6807287 | 11/1968 | Netherlands | 546/133 |
| 774858 | 5/1957 | United Kingdom | 546/124 |
| 1293446 | 10/1972 | United Kingdom | 514/161 |
| 2042522 | 9/1980 | United Kingdom | 546/124 |
| 2088364 | 6/1982 | United Kingdom | 546/124 |

OTHER PUBLICATIONS

Chem. Abs. 82:156533e (1975).
Seiler, N., et al., Hoppe-Seyler's Z. Physiol. Chem., vol. 348, 768-774 (1967).
Singh, S., et al., J. Heterocyclic Chem., 16, 625 (1979).
Waters, J., Journal of Med. Chem., vol. 21, No. 7, pp. 628-633 (1978).
Cheng, C., et al., Journal of Med. Chem., vol. 25, No. 2, pp. 145-152 (1982).
Schultz, O., et al., Pharm. Zeit., No. 40, pp. 1455 and 1456.
Derwent Abstract of S. Africa 62/3640 (2/13/63).
Kasztreiner, E., et al., Acta Chim. Acad. Scien. Hung., vol. 51, pp. 327-338 (1967).
Izv. Akad. Nauk. Arm. SSR, Biol. Nauk., vol. 15, No. 12, pp. 3-14 (1962).
Chem. Abs. 59:5665g (1963).
Feher, O., et al., Acta Biologica Szeged., vol. 21, pp. 113-125 (1975).
Chem. Abs. 86:83522w (1977).
Bosse, J., et al., Naunyn-Schmiedebergs Arch. Pharmacol Exp. Path., vol. 259, pp. 34-44 (1967).
House H., et al., J. of Org. Chem., vol. 31, pp. 3482-3489 (1966).
Ohki, E., et al., Chem. Pharm. Bull., vol. 18, No. 10, pp. 2050-2057 (1970).
Mikhlina, E., et al., Khim.-Farm. Zh., vol. 7, No. 8, pp. 492-496 (1973).
Lieberman, H., et al., J. of Pharm. Sciences, vol. 57, pp. 684 and 685 (1968).
Chem. Abs. 54:22632h (1960).
Proceedings of the B.P.S., pp. 499 and 500 (Sep. 7th-9th, 1977), Fozard, J., et al.

Primary Examiner—Richard A. Schwartz
Attorney, Agent, or Firm—Gerald D. Sharkin; Robert S. Honor; Joseph J. Borovian

[57] ABSTRACT

The dicarboxylic, heterocyclic and substituted benzoic acid alkylene bridged piperidyl amides and esters are serotonin M antagonists.

9 Claims, No Drawings

AMIDES AND ESTERS CONTAINING BRIDGED PIPERIDINES AND USE AS SEROTONIN M ANTAGONISTS

This is a continuation of application Ser. No. 644,810, filed Aug. 27, 1984 now abandoned.

This invention relates to benzoic acid derivatives.

It has been proposed (see for example J. R. Fozard in Advances in Neurology Vol. 33 Raven Press New York 1982) to use compounds with serotonin antagonistic effects, i.e. 5HT blocking effects in the treatment of migraine. Particularly interesting are the compounds which antagonise the M-receptors. A particularly active compound of this type is Metoclopramide (U.S. Pat. No. 3,177,252) which J. B. Hughes in Med.J.Australia 2 No. 17, p. 580 (1977) has reported to lead to an immediate effect on a migraine attack on slow i.v. injection of 10 mg.

Subsequently further compounds with serotonin-M antagonistic effect had been described. European Publication No. 67770 describes a narrow class of tropane phenyl esters.

The present invention provides a new group of compounds which has not been specifically suggested before in the literature and which have particularly interesting pharmacological properties, for example. serotonin M antagonistic activity and anti-arrhythmic agents, e.g. as indicated by potency in the vagus nerve test mentioned hereinafter.

The present invention provides in one aspect compounds of formula I

A-B-C-D-      I wherein A is a group of formula

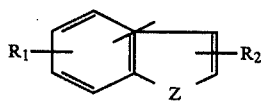

(a)

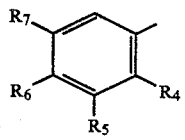

(b)

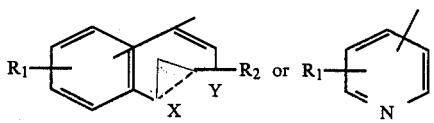

(c)            (d)

wherein the free valence is attached to either fused ring in formula (a) or (c), X-Y is —CH=CH—, —O—CH$_2$— or —N=CH—, Z is CH$_2$, —NR$_3$—, —O—, or —S—, R$_1$ and R$_2$ are independently hydrogen, halogen, (C$_{1-4}$)alkyl, (C$_{1-4}$)alkoxy, hydroxy, amino, (C$_{1-4}$)alkylamino, di(C$_{1-4}$)alkylamino, mercapto or (C$_{1-4}$)alkylthio, R$_3$ is hydrogen, (C$_{1-4}$)alkyl, (C$_{3-5}$)alkenyl, aryl or arylalkyl, R$_4$ to R$_7$ are independently hydrogen, amino, nitro, (C$_{1-4}$)alkylamino, di(C$_{1-4}$)alkylamino, halogen, (C$_{1-4}$)alkoxy, (C$_{1-4}$)alkyl, (C$_{1-4}$)alkanoylamino, pyrrolyl, sulfamoyl, or carbamoyl B is —CO— or —SO$_2$—

C is —O— or —NH—

D is a group of formula

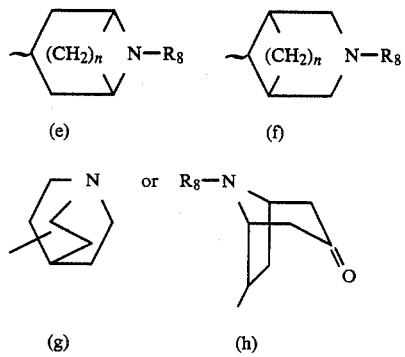

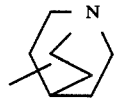
(e)

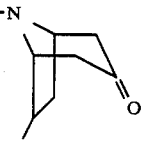
(f)

(g)            (h)

wherein R$_8$ is hydrogen, (C$_{1-7}$)alkyl, (C$_{3-5}$)alkenyl or aralkyl, and n is 2, 3 or 4 with the provisos that (1) when A is a group of formula (a) and B is —CO—, then D is other than a group of formula (e) or (g), (2) when A is a group of formula (b) wherein R$_4$ to R$_7$ are each hydrogen, B is —CO— and C is —O—, then D is other than a group of formula (f) or (h) wherein R$_8$ is methyl, (3) when A is a group of formula (d) wherein R$_1$ is hydrogen or alkoxy and B is —CO—, then D is other than a group of formula (e) wherein n is 2, (4) when A is a group of formula (d) wherein R$_1$ is hydrogen, B is CO and C is —O—, then D is other than a group of formula (g)

(5) when A is a group of formula (b), B is —CO— and D is (e) or (g), then at least one of R$_4$ to R$_7$ in the formula (b) is sulfamoyl or carbamoyl, their acid addition salts and quaternary ammonium salts, hereinafter referred to as compounds of the invention.

Any alkyl moiety preferably is methyl, ethyl or propyl. Alkoxy is preferably methoxy or ethoxy. Aralkyl is conveniently aryl(C$_{1-4}$)alkyl. Alkenyl is preferably allyl or methallyl. Any aryl moiety is preferably unsubstituted phenyl or phenyl mono- or poly-substituted by (C$_{1-4}$)alkyl, e.g. methyl, halogen, e.g. fluorine, hydroxy, or (C$_{1-4}$)alkoxy, e.g. methoxy. Preferably any substituted aryl group is mono-substituted. Aralkyl is conveniently benzyl. Halogen is fluorine, chlorine, bromine or iodine.

A is conveniently a group of formula (a). In the group of formula (a), the group -B- may be attached to the ring carbon atom in position 2,3,4,5,6 or 7 of the nucleus, but preferably in position 4 and 5. Most preferably the -B- group is attached to the ring containing Z, especially in position 3. Preferably A is indole.

R$_1$ is attached to the ring carbon atom in position 4,5,6 or 7 of the nucleus, preferably position 5 and R$_2$ is attached to the ring carbon atom in position 2 or 3 of the nucleus. Tautomers are also covered by formula I e.g. when R$_2$ is hydroxy or mercapto in the 2 position. R$_3$ is conveniently hydrogen or alkyl.

In a group of formula (b) preferably one of R$_4$ to R$_7$ is other than hydrogen, and/or R$_4$ is hydrogen, or (C$_{1-4}$)alkyl and/or R$_5$ is hydrogen or halogen or carbamoyl and/or R$_6$ is hydrogen or (C$_{1-4}$)alkyl and/or R$_7$ is hydrogen, halogen or sulphamoyl.

Examples of the group of formula (b) include 2-methoxy-phenyl, p-tolyl, 3-carbamoylphenyl, 3-sulphamoylphenyl, 3,5-dimethylphenyl or 3,5-dichlorophenyl.

If A is a group of formula (c) wherein X-Y is —CH=CH—, the free valence is preferably in position 2,3,6 or 7 of the nucleus. $R_1$ is preferably in position 6 or 7. $R_2$ is preferably in position 2 or 3. $R_2$ may replace one of the H atoms in X-Y.

If A is a group of formula (c) wheren X-Y is —O—CH$_2$—, or —N=CH—, the N or O atom is in position 1, the free valence is preferably in position 2,3,6 or 7. $R_2$ is preferably in position 2 or 3. $R_2$ may replace one hydrogen in X-Y.

If A is a group of formula (d), then the free valence is preferably in position 3 or 4. $R_1$ is preferably in position 2.

The group of formula (e) may exist in two different configurations namely:

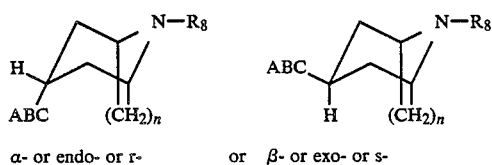

α- or endo- or r-     or     β- or exo- or s-

The two different configurations may be appreciated by making the groups of formula (e) have a configuration wherein a reference plane may be drawn through the carbon atoms of the piperidyl ring and the nitrogen atom is above the plane and the alkylene bridge is below the plane. The group of formula (e) has the α-configuration when the group ABC is below the plane on the same side as the alkylene bridge. This corresponds to the endo configuration and also to the configuration in tropine etc. The group of formula (e) has the β-configuration when it is above the plane on the same side as the nitrogen bridge. This corresponds to the exo configuration and also the configuration in pseudotropine etc. Used hereinafter is the exo/endo nomenclature. The endo isomers are preferred.

The group of formula (f) may exist in two different configurations:

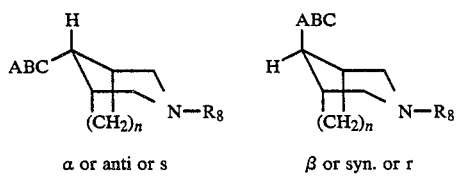

α or anti or s     β or syn. or r

In the anti configuration the group ABC is oriented away from the nitrogen atom and in the syn configuration is oriented towards the nitrogen atom (see Chemical abstracts, Index Guide 1982 p 1701). In Org. Chem. 35 2840 and 2867 (1970) the configuration of the carbon to which the group ABC is bound is designated r or s. Hereinafter the syn/anti nomenclature is used.

The preferred configuration is anti.

A group of formula g is also known as quinuclidinyl. Conveniently this is 3- or 4-quinuclidinyl and especially 3-quinuclidinyl.

The group of formula (h) may exist in two configurations which are diastereoisomers:

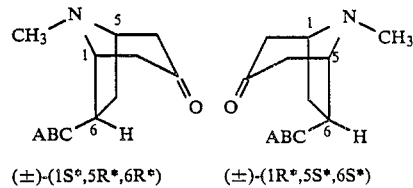

(±)-(1S*,5R*,6R*)     (±)-(1R*,5S*,6S*)

In the groups of formula (e), (f) and (h), $R_8$ is preferably alkyl especially methyl.

B is preferably CO.

C is preferably O.

A group of compounds comprises compounds of formula Ia

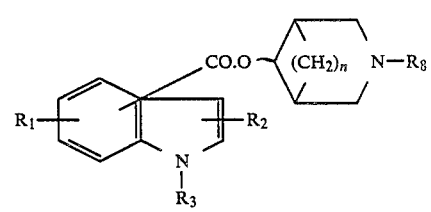

wherein the carbonyl group is attached to either fused ring, and $R_1$, $R_2$, $R_3$, $R_8$ and n are as defined above, as well as acid addition salts and quaternary ammonium salts thereof.

Another group of compounds comprises compounds of formula Ib

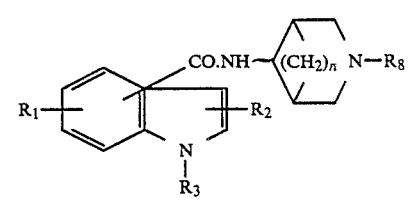

wherein the carbonyl group is attached to either fused ring, and $R_1$, $R_2$, $R_3$, $R_8$ and n are as defined above, as well as acid addition salts and quaternary ammonium salts thereof.

A group of compounds comprises compounds of formula Ic

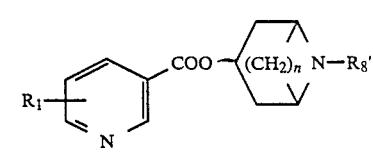

wherein $R_1$ and n are as defined above and $R_8'$ is hydrogen or (C$_{1-4}$)alkyl, as well as acid addition salts and quaternary ammonium salts thereof.

A group of compounds comprises compounds of formula Id

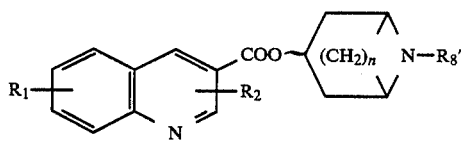

wherein $R_1$, $R_2$, n and $R_8^1$ are as defined above, as well as acid addition salts and quaternary ammonium salts thereof.

A group of compounds comprises compounds of formula Ie

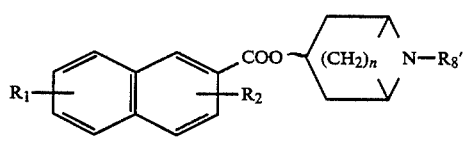

wherein $R_1$, $R_2$, n and $R_8^1$ are as defined above, as well as acid addition salts and quaternary ammonium salts thereof.

A group of compounds comprises compounds of formula If

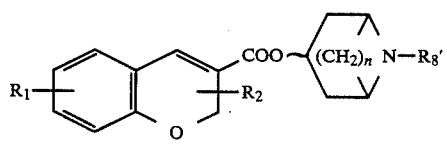

wherein $R_1$, $R_2$, n and $R_8^1$ are as defined above, as well as acid addition salts and quaternary ammonium salts thereof.

A group of compounds comprises compounds of formula Ig

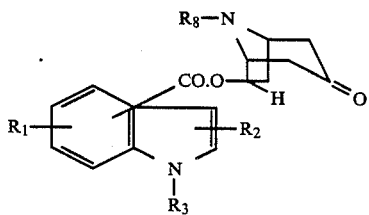

wherein the carbonyl group may be attached to either fused ring and $R_1$, $R_2$, $R_3$, $R_8$ and n are as defined above, as well as acid addition salts and quaternary ammonium salts thereof.

A group of compounds comprises compounds of formula Ih

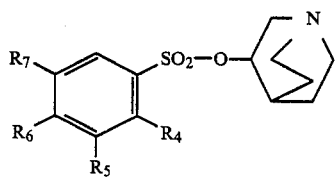

wherein $R_4$ to $R_7$ are as defined above, as well as acid addition salts and quaternary ammonium salts thereof.

A group of compounds comprises compounds of formula Ii

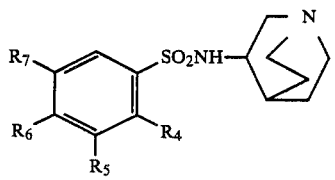

wherein $R_4$ to $R_7$ are as defined above, as well as acid addition salts and quaternary ammonium salts thereof.

Another group of compounds comprises compounds of formula I wherein

A is a group of formula (c) or (d)

B is CO

D is a group of formula (e) or (g) as well as acid addition salts and quaternary ammonium salts thereof.

A further group of compounds comprises compounds of formula I wherein

A is a group of formula (a), or a group of formula (b) wherein each of $R_4$ to $R_7$ is other sulfamoyl or carbamoyl B is CO D is a group of formula (f), as well as acid addition salts and quaternary ammonium salts thereof. In a further sub-group in the formula (a), $R_1$ and $R_2$ are other than alkyl.

In the all above sub-groups of formula I compounds the provisos to formula I also apply.

In particular the present invention provides a process for the production of a compound of formula I as well as acid addition salts thereof or quaternary ammonium salts thereof which includes the step of (a) condensing an appropriate compound of formula II $$A-B-OH \qquad II$$

wherein A and B are as defined above, a reactive derivative thereof, or a precursor of the acid or derivative, with an appropriate compound of formula III $$H-C-D \qquad III$$

wherein C and D are as defined above, or a precursor of the compound or, (b) alkylating a compound of formula I having a secondary amino group to produce a compound of formula I with a tertiary amino group, (c) deprotecting any protected form of a compound of formula I to obtain a compound of formula I, (d) halogenating a compound of formula I wherein A is a group of formula (a) and $R_2$ is hydrogen to obtain the corresponding compound wherein $R_2$ is halogen, or (e) alkoxylating a compound of formula I wherein A is a group of formula (a) and $R_2$ is halogen to obtain the corresponding compound wherein $R_2$ is alkoxy, and recovering the resultant compound of formula I as such or as acid addition salt or as a quaternary ammonium salt thereof.

It is assumed that in all these reaction processes the configuration of the groups of formula (e), (f) and (h) remain unchanged.

The condensation process of the invention to obtain amides and esters may be effected in conventional manner for analogous compounds.

For example, the carboxylic acid group may be activated in the form of a reactive acid derivative, especially for the production of amides.

Suitable reactive acid derivatives may be formed as in situ intermediates by reaction with N,N'-carbonyl-diimidazole or with N-hydroxy-succinimide. Alternatively an acid chloride may be used, e.g. produced by reaction with oxalyl chloride. In the case of sulphonic acids, the acid chloride is preferably used.

For production of esters, the alcohol may be used e.g. in the form of an alkali metal salt, preferably the lithium salt. Such salts may be produced in conventional manner, e.g. by reaction of a n-butyl lithium with the alcohol in tetrahydrofuran. If desired a heterocyclic or tertiary amine, e.g. pyridine or triethylamine, may be present, especially for the production of amides.

Suitable reaction temperatures may be from about −10° to about 100°.

Other suitable inert organic solvents include, e.g. tetrahydrofuran or dimethoxyethane.

The compounds of the invention may be converted into other compounds of the invention, e.g. in conventional manner. Some interconversions are exemplified in processes (b), (c), (d) and (e).

The alkylation reaction of process (b) may be effected in conventional manner. Any free amino group may be alkylated, especially compounds of formula (a) wherein Z is NH. Appropriate alkylation conditions include reaction with an alkyl halide in the presence of a sodium alcoholate. Suitable temperatures may be from about −50° to about −30° C.

The deprotection reaction of process (c) is specifically suitable for the production of compounds with secondary amino groups, e.g. $R_8 = H$ in the group of formulae (e), (f) and (h) or primary amino groups of formula (b), e.g. $R_6 = NH_2$.

For example a compound of formula I may be produced in protected form, e.g. $R_8$ being replaced by a secondary amino protecting group such as benzyl.

The benzyl group may be split off in conventional manner, e.g. by hydrogenation to produce the corresponding compound of formula I wherein $R_8$ is hydrogen.

Suitably the hydrogenation may be effected in the presence of palladium on active charcoal at room temperature or at a slightly elevated temperature. Suitable solvents include acetic acid, ethyl acetate or ethanol.

A primary amino group as $R_6$ may be protected by e.g. N-benzyloxycarbonyl. This group may be split off by hydrogenation analogously to that indicated above. In the presence of a benzyl group the N-benzyloxycarbonyl group is generally split off first so that this group may be selectively split off.

Also the amino group may be in the form of a nitro group. This can be selectively reduced in conventional manner, e.g. by iron in hydrochloric acid.

Halogenation according to process (d) may be effected in conventional manner. For example with N-chloro-succinimide may lead to chlorination. Such reactions may be effected in a suspension in chloroform. Reaction with N-iodo-succinimide may alternatively lead to iodination.

Replacement of reactive halogen groups according to process (e) may be effected in conventional manner e.g. by reaction with a appropriate alcohol at e.g. room temperature from 10 to 20 hours at least.

A precursor of a starting material may be employed if desired. Such a precursor may be capable of being converted into the starting material in conventional manner but instead the process of the invention is carried out with the precursor and the other starting material or materials or a precursor thereof. The resultant product is converted into the compound of the invention in conventional manner, e.g. by using the same reaction conditions by which the precursor may be converted into the starting material. Typical precursors include protected forms of a starting material, e.g. wherein amino groups are temporarily protected.

The compounds of the invention may be isolated and purified in conventional manner. If isomeric mixtures of starting materials containing groups of formula (e), (f) and (h) are used then the final compounds may be purified by e.g. column chromatography.

Compounds of formula III wherein C is —NH— and D is a group of formula (f) are new and form part of the present invention. The compounds have never been specifically suggested before although they fall under various generic disclosures.

The compounds are useful intermediates by virtue of the functional groups present therein, e.g. the amino group, e.g. for the preparation of a wide range of pharmacologically active compounds, e.g. amides as described herein which have an interesting pharmacological profile and have never been disclosed as Serotonin M antagonists and other activities disclosed hereinafter.

These compounds of formula III may for example be produced by reduction of the corresponding oxime, in analogous manner to other known compounds of formula III.

The above reduction may be effected, e.g. by catalytic hydrogenation, e.g. over platinum (believed to lead primarily to anti isomers), Bouveault-Blanc reaction procedures, e.g. sodium/amyl alcohol or butanol (believed to lead primarily to isomers), or aluminium hydride procedures or sodium borohydride (also leading primarily to the anti isomers).

Any mixture of syn and anti forms may be separated by chromatography.

Compounds of formula III wherein B is —O— are known and may be produced in conventional manner by reduction of the corresponding ketone.

Other compounds of formula III are in general known. Insofar as the production of a starting matrial is not particularly described herein, it is known, or may be produced in analogous manner to known compounds, in analogous manner to that described herein, e.g. the examples, or to known procedures for analogous compounds.

Free base forms of compounds of the invention may be converted into salt forms. For example acid addition salts may be produced in conventional manner by reacting with a suitable acid, and vice versa. Suitable acids for salt formation include hydrochloric acid, malonic acid, hydrobromic acid, maleic acid, malic acid, fumaric acid, methanesulphonic acid, oxalic acid, and tartaric acid. Quaternary ammonium salts of the compounds of the invention may be produced in conventional manner, e.g. by reaction with methyl iodide.

In the following examples all temperatures are in degrees Centigrade and are uncorrected.

The configuration of the title compounds of Examples 1 and 2 have been confirmed by x-ray analysis. The configuration of the remaining compounds is believed to follow that of the starting materials of formula III which were used pure, except where otherwise stated.

EXAMPLE 1

Indol-3-yl carboxylic acid-9-anti-3-methyl-3-azabicyclo[3.3.1]non-9-yl amide

(a) Indol-3-yl carboxylic acid chloride 32.2 g (0.2M) dry indol-3-yl carboxylic acid are suspended in 150 ml absolute methylene chloride. 26 ml oxalyl chloride are added to the stirred mixture at 20° C. over 30 minutes. Gas evolution results. The mixture is stirred for 3½ hours at 20° C. 150 ml Hexane are added. The mixture stirred for another 20 minutes and the resultant heading compound filtered off, washed with methylene chloride/hexane 1:1 dried at 20° in a vacuum to give beige crystals, M.pt. 135°-136° (decomp) which are used further without purification.

(b) 3-methyl-3-aza-bicyclo[3.3.1]nonan-9-one oxime 51 g sodium acetate dihydrate and 26.5 g hydroxylamine hydrochloride are pounded in a mortar to a thin paste. 300 ml methanol are added and the mixture filtered off. The filtrate is treated with 30.6 g 3-methyl-3-azabicyclo[3.3.1]nonan-9-one and 500 ml methanol is added. The resultant suspension is stirred for 2½ hours at 50° C. About half the methanol is evaporated. The residue is adjusted with potassium hydrogen carbonate solution to pH 8 and extracted with chloroform, and three times with chloroform containing 10% isopropanol. The combined organic phases are dried and concentrated to give the crystalline heading compound. M.pt. 111°-112°.

(c) 9-anti-3-methyl-3-aza-bicyclo[3.3.1]non-9-yl amine

A solution of 9.6 g (100%) sulphuric acid in 30 ml absolute tetrahydrofuran are added to a cooled and stirred mixture of 13.5 g lithium aluminium hydride in 140 ml absolute tetrahydrofuran at −10° to 0° C. within 45 minutes. The mixture is allowed to stand for 2 hours. A solution of 14.1 g 3-methyl-3-aza-bicyclo[3.3.1]nonan-9-one oxime in 130 ml absolute tetrahydrofuran is added in a thin stream over 30 hours to the stirred mixture at 20°-30° C. and allowed to react further at 40° for 3 hours and overnight for 15 hours (overnight) at room temperature. To work up the reaction mixture is cooled to −15° to 0° C. and a mixture of 40 ml water in 40 ml tetrahydrofuran is added carefully. The mixture is allowed to react at room temperature. The mixture is filtered off. The residue is washed twice with tetrahydrofuran. The organic phases are combined, dried in a low vacuum (400 mm Hg). The residue is distilled.

1st Fraction (10 mm Hg and 80°-88°) n=1.4620
2nd Fraction (8 mm Hg and 87°-88°) n=1.5050
3rd Fraction (8 mm Hg and 88°) n=1.5050

(All specific refractive indexes measured at 20° and the D line) Fractions 2 and 3 contain the heading compound.

(d) Indol-3-yl carboxylic acid-9-anti-3-methyl-3-azabicyclo[3.3.1]-non-9-yl amide 5 ml pyridine and then a solution of 5.5 g 9-anti-3-methyl-3-aza-bicyclo[3.3.1]non-9-yl amine in 25 ml absolute methylene chloride are added dropwise to a stirred suspension of 5.4 g indol-3-yl carboxylic acid chloride (produced in step a) in 25 ml absolute methylene chloride at −15° to −5° C.

The resultant mixture is stirred at room temperature for 20 hours, and partitioned between methylene chloride and 1N to 2N aqueous sodium carbonate. The organic phases are combined, concentrated and the resultant precipitate filtered off. The filtrate is concentrated further to give a bright yellow foam, which is dissolved in methylene chloride containing 4% methanol and 0.2% ammonia and chromatographed on 250 g silicagel with this solution.

Fractions obtained
1st 1.3 g less unpolar substances (thrown away)
2nd 900 mg Fraction: uniform on t.l.c.
3rd 700 mg Fraction: mixture
4th 1.95 g Fraction 3: uniform on t.l.c.

The pore polar fraction (4) contains the title compound which is crystallized twice from ethyl acetate/hexane. M.pt. 173°-175° C.

In analogous manner the following compounds of formula I are obtained:

| Example | A | | | | | B | Position of B | C | D | Position of g | Configuration | n | R$_8$ | M. pt. |
|---|---|---|---|---|---|---|---|---|---|---|---|---|---|---|
| | | R$_1$ | R$_2$ | X—Y | Z | | | | | | | | | |
| 2 | (a) | H | H | — | NH | CO | (3) | O | (f) | | anti | 3 | CH$_3$ | 197-198° |
| 3 | (a) | H | H | — | NH | CO | (3) | O | (f) | | syn | 3 | CH$_3$ | 188-189° |
| 4 | (c) | H | H | N=CH | — | CO | (3) | O | (e) | | endo | 3 | CH$_3$ | 99-101° |
| 5 | (d) | H | — | — | — | CO | (3) | O | (e) | | endo | 3 | CH$_3$ | 190°(1)(2) |
| 6 | (c) | H | H | CH=CH | — | CO | (2) | O | (e) | | endo | 3 | CH$_3$ | 83-84° |
| 7 | (c) | H | H | O—CH$_2$ | — | CO | (3) | O | (e) | | endo | 3 | CH$_3$ | 139-141°(1)(3) |
| 8 | (a) | H | H | — | NH | CO | (3) | O | (h) | | (1S*, 5R*, 6R*) | — | CH$_3$ | 188-189° |
| | | R$_4$ | R$_5$ | R$_6$ | R$_7$ | | | | | | | | | |
| 9 | (b) | H | H | CH$_3$ | H | SO$_2$ | — | O | (g) | 3 | RS | — | — | 164-166° |
| 10 | (b) | H | H | CH$_3$ | H | SO$_2$ | — | NH | (g) | 3 | RS | — | — | 158-159.5° |
| 11 | (b) | H | $\underset{\diagdown C-NH_2}{\overset{O}{\parallel}}$ | H | H | CO | — | NH | (g) | 3 | RS | — | — | 203-205° |
| 12 | (b) | OCH$_3$ | H | H | SO$_2$NH$_2$ | CO | — | NH | (g) | 3 | RS | — | — | from 235°(1) |
| 13 | (b) | H | H | H | SO$_2$NH$_2$ | CO | — | NH | (g) | 3 | RS | — | — | 258-261°(1) |

(1)Decomposition
(2)hydrogen Oxalate
(3)hydrogen maleate

In analogous manner the following compounds of formula I may also be produced.

| Example | A | | | | | B | position of B | C | D | position of g | n | $R_8$ |
|---|---|---|---|---|---|---|---|---|---|---|---|---|
| | | $R_1$ | $R_2$ | X---Y | Z | | | | | | | |
| 14 | (a) | 5-Cl | 2-OCH$_3$ | — | S | SO$_2$ | 3 | NH | (g) | 4 | — | — |
| 15 | (a) | 6-CH$_3$ | 3-Cl | — | O | CO | 4 | O | (f) | — | 2 | C$_3$H$_7$ |
| 16 | (a) | 7-S—CH$_3$ | 2-CH$_3$ | — | CH$_2$ | SO$_2$ | 5 | O | (h) | — | — | C$_2$H$_5$ |
| 17 | (a) | 5-OH | 3-CH$_3$ | — | O | CO | 4 | NH | (f) | — | 2 | C$_2$H$_4$ |
| 18 | (a) | 4-NH$_2$ | 2-SCH$_3$ | — | N—CH$_3$ | SO$_2$ | 5 | O | (g) | 3 | — | — |
| 19 | (a) | 4-N(CH$_3$)$_2$ | 2-Cl | — | S | CO | 6 | NH | (h) | — | — | BZ |
| 20 | (c) | 5-NHCH$_3$ | 3-F | CH=CH | — | SO$_2$ | 2 | O | (g) | 4 | — | — |
| 21 | (c) | 6-F | 2-Cl | O—CH$_2$ | — | CO | 7 | NH | (e) | — | 2 | p-Cl—BZ |
| 22 | (c) | 8-CH$_3$ | 3-OCH$_3$ | N=CH | — | SO$_2$ | 6 | O | (e) | — | 3 | CH$_3$ |
| 23 | (d) | 5-Cl | — | — | — | CO | 3 | NH | (h) | — | — | — |
| 24 | (d) | 6-OCH$_3$ | — | — | — | SO$_2$ | 4 | O | (g) | 3 | — | — |
| 25 | (d) | 4-CH$_3$ | — | — | — | CO | 3 | NH | (f) | — | 4 | CH$_3$ |
| 26 | (d) | 6-NHCH$_3$ | — | — | — | SO$_2$ | 4 | O | (e) | — | 2 | i-Prop. |
| | | $R_4$ | $R_5$ | $R_6$ | $R_7$ | | | | | | | |
| 27 | (b) | Cl | F | OC$_2$H$_5$ | NHCOCH$_3$ | SO$_2$ | | O | (h) | — | — | C$_3$H$_7$ |
| 28 | (b) | CH$_3$ | N—(CH$_3$)$_2$ | NO$_2$ | CH$_3$O | CO | | O | (f) | — | 3 | BZ |
| 29 | (b) | NH$_2$ | Pyrrolyl | C$_2$H$_5$O | C$_3$H$_7$ | SO$_2$ | | NH | (e) | — | 4 | C$_4$H$_9$ |
| 30 | (b) | H | C$_4$H$_9$ | NHCH$_3$ | N(C$_2$H$_5$)$_2$ | CO | | O | (f) | — | 3 | CH$_3$ |
| 31 | (b) | NO$_2$ | Cl | NHC$_3$H$_7$ | C$_2$H$_5$ | SO$_2$ | | O | (h) | — | — | C$_3$H$_6$ |
| 32 | (b) | F | CH$_3$O | NHCOC$_2$H$_5$ | Pyrrolyl | SO$_2$ | | NH | (g) | 3 | — | — |
| 33 | (b) | SO$_2$NH$_2$ | H | $\underset{NH_2}{\overset{O}{\underset{\|}{C}}}$ | C$_3$H$_7$ | CO | | O | (e) | — | 2 | CH$_3$ |
| 34 | (b) | H | CH$_3$O | SO$_2$NH$_2$ | C$_2$H$_5$ | CO | | NH | (e) | — | 4 | C$_3$H$_7$ |
| 35 | (b) | OCH$_3$ | F | NHCOCH$_3$ | SO$_2$NH$_2$ | SO$_2$ | | NH | (h) | — | — | C$_2$H$_5$ |

The compounds of the invention exhibit pharmacological activity and are therefore useful as pharmaceuticals, e.g. for therapy.

In particular the compounds exhibit serotonin M receptor antagonist activity as indicated in standard tests. For example, in one test the action of the compounds in inhibiting the action of serotonin in reducing the amplitude of the compound action potential from the isolated rabbit vagus nerve was observed according to the principles of Riccioppo Neto, European Journal of Pharmacology (1978) 49 351-356, under conditions permitting differentation between action potentials generated in myelinatd nerve fibres (A fibres) and those generated in small non-myelinated fibres (C fibres) as described by B. Oakley and R. Schater, Experimental Neurobiology, A Laboratory Manual, University of Michigan Press, 1978, p.85 to 96. Serotonin itself exerts its effect selectively on the C-fibres progressively with dosage. This action of serotonin is not blocked by the known serotonin antagonists, metitepine, methysergide, BOL - 148, which have been said to block D receptors for serotonin, but not M receptors (see Gaddam and Picarlli, Brit.J.Pharmacol. (1957), 12, 323-328). It therefore appears that serotonin reduces the amplitude of the action potential carried by the C fibres through an effect mediated by M receptors for serotonin which are located on these nerve fibres.

The test may be effected by establishing a dose response curve for serotonin ($10^{-7}$—$5 \times 10^{-6}$ M) after setting up the nerve. The serotonin is washed out and when the C fibre action potential has regained its original amplitude the compound of the invention at a set concentration of from about $10^{-10}$ M to about $10^{-6}$ M is preincubated with the nerve for 30 to 60 minutes. Varying concentrations of serotonin ($10^{-7}$ to $10^{-4}$ M) are then applied with the compound of the invention at the concentration as was present during the preincubation period.

The M receptor antagonists of the invention either entirely block the action of serotonin (non-competitive antagonist) or cause a parallel shift of the serotonin/dose response curve to the right (i.e. increased concentrations of serotonin were required for effect) (competitive antagonist). The $pD'_2$ or $pA_2$ value may be obtained in the conventional manner.

The serotonin M receptor antagonist activity is also indicated by inhibiting the effect of serotonin on the isolated rabbit heart according to the rethod of J. R. Fozard and A. T. Moborak Ali, European Journal of Pharmacology, (1978), 49, 109-112 at concentrations of $10^{-11}$ to $10^{-5}$ M of the compound of the invention. $pD'_2$ or $pA_2$ values may be calculated in the conventional manner.

The action of the compounds as serotonin M receptor antagonists for the treatment of analgesia is confirmed by action in the hot plate test at a dose of from about 0.1 to 100 mg/kg s.c. or p.o.

The serotonin M receptor antagonist activity is furthermore indicated in the cantharidine blister base test at a concentration of about $10^{-8}$ M. A blister is produced on the skin of the forearm of human volunteers with cantharidine. When serotonin is applied to the base of such blisters it produces pain which can be measured, the intensity being proportional to the concentration of serotonin applied. The procedure has been described by C. A. Keele and D. Armstrong in Substances producing Pain and Itch, Edward Arnold, London, 1964, p. 30 to 57. This algesic action of serotonin is not inhibited by the serotonin D receptor antagonists such as lysergic acid diethylamide or its bromo derivative and is therefore believed to be mediated by M receptors.

In the procedure followed, the area under the curve instead of the peak amplitude is measured by a linear integrator coupled to a pain intensity indicator which is operated by the volunteer. With increasing concentrations of serotonin a cumulative dose-response curve to serotonin may be obtained. When no further response on increasing the serotonin concentration is obtained, the serotonin is washed off and the blister incubated with physiological buffer solution for at least 40 minutes before the compound of the invention is applied. The test substance is preincubated with the blister base for 30 minutes at a concentration of about $10^{-8}$ M before varying concentrations of serotonin are applied. A $pA_2$ value may be obtained in the conventional manner.

The compounds of the invention are therefore useful as serotonin M receptor antagonists, e.g. for the treatment of pain, especially migraine, vascular and cluster headaches and trigeminal neuralgia and also for the treatment of heart circulation disorders, e.g. for the treatment of sudden death, and possibly as antipsychotics.

For this use the dosage will, of course, vary depending on the compound employed, mode of administration and treatment desired. However, in general, satisfactory results are obtained when administered at a daily dosage of from about 0.1 mg to about 40 mg per kg animal body weight, conveniently given in divided doses 2 to 4 times a day or in sustained release form. For the larger mammals, the total daily dosage is in the range from about 0.5 to about 500 mg, and dosage forms suitable for oral administration comprise from about 0.2 mg to about 250 mg of the compounds admixed with a solid or liquid pharmaceutical carrier or diluent.

The compounds of the invention furthermore exhibit anti-arrhymic activity as indicated by their serotonin M receptor antagonist activity and in standard tests. For example the compounds inhibit arrhythmias induced by norepinephrine in anaesthetized rats. In this test infusions of norepinephrine (3 to 10 microgram/animal body weight) are given until an arrhythmic phase as indicated by ECG measurements lasts longer than 10 seconds. After control of 3 consecutive injections of norephinephrine the compound of the invention is injected at 10 from about 10 to about 500 microgram/kg animal body weight followed by norepinephrine injections The arrhythmic phase is reduced, or abolished depending on the dose of test compound.

The compounds are therefore useful as anti-arrhythmic agents.

For this use the dosage will, of course, vary depending on the compound employed, mode of administration and treatment desired. However, in general, satisfactory results are obtained when administered at a daily dosage of from about 10 micrograms to about 10 milligrams per kg animal body weight, conveniently given in divided doses 2 to 4 times a day or in sustained release form. For the larger mammals, the total daily dosage is in the range from about 0.5 to about 500 mg, and dosage forms suitable for oral or conveniently intravenous administration comprise from about 0.2 mg to about 250 mg of the compound admixed with a solid or liquid pharmaceutical carrier or diluent.

The present invention accordingly provides a compound of the invention in pharmaceutically acceptable form, e.g. in free base form, or pharmaceutically acceptable acid addition salt form or quaternary ammonium salt form, for use as a pharmaceutical, particularly for use as a serotonin M antagonist for those diseases where blockage of serotonin M receptors would be expected to have beneficial effects, e.g. as an analgesic agent, especially as an anti-migraine agent and as an anti-arrhythmic agent.

The preferred indication is the analgesic indication. The preferred compounds are the title compounds of Examples 1 and 2.

The compounds of the invention may be administered in free base form, or in pharmaceutically acceptable salt form, e.g. suitable acid addition salts and quaternary ammonium salts Such salts exhibit the same order of activity as the free bases. The present invention accordingly also provides a pharmaceutical composition comprising a compound of the invention, in free base form or an acid addition salt thereof or a quaternary ammonium salt thereof, in association with a pharmaceutical carrier or diluent. Such compositions may be formulated in conventional manner so as to be for example a solution or a tablet.

The compounds of the invention may be administered in analogous manner to that used for known standards for the relevant utility, e.g. metoclopramide as anti-migraine agents. The exact dose for a particular compound will depend on a number of factors, in particular the relevant potency. For example the preferred compound of this invention, the Example 2 compound has been found to have a $pA_2$ of 8.2 in the above vagus nerve test where-as metoclopramide has a $pH_2$ of 7.3. It is thus indicated that this compound may be administered at the same or lower doses as metoclopramide.

In a 1st group of compounds Z is —$CH_2$—.
In a 2nd group of compounds Z is —$NR_3$—.
In a 3rd group of compounds Z is —O—.
In a 4th group of compounds Z is —S—.
In a 5th group $R_1$ or $R_2$ is hydrogen.
In a 6th group $R_1$ or $R_2$ is halogen.
In 7th group $R_1$ or $R_2$ is alkyl.
In a 8th group $R_1$ or $R_2$ is alkoxy.
In a 9th group $R_1$ or $R_2$ is hydroxy.
In a 10th group $R_1$ or $R_2$ is amino.
In a 11th group $R_1$ or $R_2$ is alkylamino.
In a 12th group $R_1$ or $R_2$ is dialkylamino.
In a 13th group $R_1$ or $R_2$ is mercapto.
In a 14th group $R_1$ or $R_2$ is alkylthio.
In a 15th group $R_3$ is hydrogen.
In a 16th group $R_3$ is alkyl.
In a 17th group $R_3$ is alkenyl.
In a 18th group $R_3$ is aryl.
In a 19th group $R_3$ is arylalkyl.
In a 20th group one of $R_4$ to $R_7$ is hydrogen.
In a 21st group one of $R_4$ to $R_7$ is amino.
In a 22nd group one of $R_4$ to $R_7$ is nitro.
In a 23rd group one of $R_4$ to $R_7$ is alkylamino.
In a 24th group one of $R_4$ to $R_7$ is dialkylamino,
In a 25th group one of $R_4$ to $R_7$ is halogen.
In a 26th group one of $R_4$ to $R_7$ is alkoxy.
In a 27th group one of $R_4$ to $R_7$ is alkyl.
In a 28th group one of $R_4$ to $R_7$ is alkanoylamino.
In a 29th group one of $R_4$ to $R_7$ is pyrrolyl.
In a 30th group one of $R_4$ to $R_7$ is sulfamoyl.
In a 31st group one of $R_4$ to $R_7$ is carbamoyl.
In a 32nd group of compounds B is —CO—.
In a 33rd group of compounds B is —$SO_2$.
In a 34th group of compounds C is —O—.
In a 35th group of compounds C is —NH—.
In a 36th group $R_8$ is hydrogen.
In a 37th group $R_8$ is alkyl.
In a 38th group $R_8$ is alkenyl.
In a 39th group $R_8$ is aralkyl.
In a 40th group X-Y is CH—CH.

In a 41st group X-Y is O=CH$_2$.
In a 42nd group X-Y is N=CH.

What we claim is:

1. A compound of formula A-B-C-D wherein A is a group of formula (a)

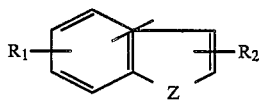

wherein the free valence is attached to either of the fused rings,

Z is —CH$_2$—, —NR$_3$—, —O— or —S—;

R$_1$ and R$_2$, independently, are hydrogen, halogen, (C$_{1-4}$)alkyl, (C$_{1-4}$)alkoxy, hydroxy, amino, (C$_{1-4}$)alkylamino, di-(C$_{1-4}$)alkylamino, mercapto or (C$_{1-4}$)alkylthio;

R$_3$ is hydrogen, (C$_{1-4}$)alkyl, (C$_{3-5}$)alkenyl, unsubstituted phenyl, phenyl mono- or polysubstituted by (C$_{1-4}$)alkyl, halogen, hydroxy or (C$_{1-4}$)alkoxy, or unsubstituted phenyl (C$_{1-4}$)alkyl;

B is —CO— or —SO$_2$—;

C is —O— or —NH—; and

D is a group of formula (f)

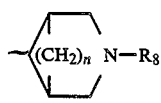

where R$_8$ is hydrogen, (C$_{1-7}$)alkyl, (C$_{3-5}$)alkenyl unsubstituted phenyl(C$_1$-4)alkyl/mono- or poly-substituted on the phenyl moiety thereof by (C$_{1-4}$)alkyl, halogen, hydroxy or (C$_{1-4}$)alkoxy; and n=2, 3 or 4 or a pharmaceutically acceptable acid addition or quaternary ammonium salt thereof.

2. A compound of claim 1 wherein B is CO or a pharmaceutically acceptable acid addition salt or a quaternary ammonium salt thereof.

3. A compound of claim 2 wherein R$_1$ and R$_2$ are each other than alkyl or a pharmaceutically acceptable acid addition salt or a quaternary ammonium salt thereof.

4. A compound of claim 1 having the formula Ia

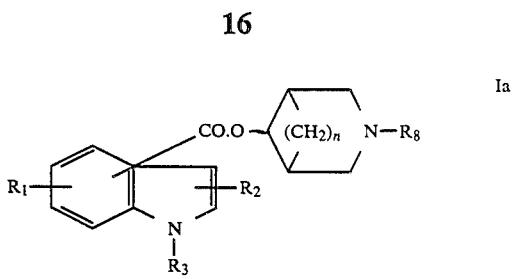

wherein the carbonyl group is attached to either of the fused rings, and R$_1$, R$_2$, R$_3$, R$_8$ and n are as defined in claim 1, or a pharmaceutically acceptable acid addition or quaternary ammonium salt thereof.

5. A compound of claim 1 having the formula Ib

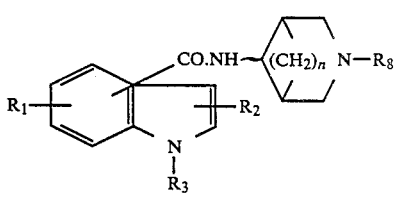

wherein the carbonyl group is attached to either of the fused rings, and R$_1$, R$_2$, R$_3$, R$_8$ and n are as defined in claim 1, or a pharmaceutically acceptable acid addition or quaternary ammonium salt thereof.

6. A compound of claim 5 which is indol-3-yl carboxylic acid 9-anti-3-methyl-3-azabicyclo non-9-yl amide or a pharmaceutically acceptable addition salt or a quaternary ammonium salt thereof.

7. A compound of claim 1 wherein Z is —NH—; R$_1$ and R$_2$ are hydrogen; B is —CO— and is attached to formula (a) in the 3-position; C is —O—; formula (f) is in the anti-configuration; R$_8$ is CH$_3$; and n is 3; or a pharmaceutically acceptable acid addition or quaternary ammonium salt thereof.

8. A pharmaceutical composition useful for inducing a serotonin M receptor antagnoist effect comprising a pharmaceutically acceptable carrier or diluent and a therapeutically effective amount of a compound of claim 1, or a pharmaceutically acceptable acid addition or quaterary ammonium salt thereof.

9. A method of inducing a serotonin M receptor antagonist effect comprising administering to a subject in need of such treatment a therapeutically effective amount of a compound of claim 1, or a pharmaceutically acceptable acid addition or quaternary ammonium salt thereof.

* * * * *